United States Patent [19]

Nelson

[11] 4,093,808

[45] June 6, 1978

[54] PRODUCTION OF CYANURIC ACID FROM UREA

[75] Inventor: George D. Nelson, Creve Coeur, Mo.

[73] Assignee: Monsanto Company, St. Louis, Mo.

[21] Appl. No.: 752,380

[22] Filed: Dec. 20, 1976

[51] Int. Cl.$^2$ .......................................... C07D 251/32
[52] U.S. Cl. .................................................. 544/192
[58] Field of Search ................... 260/248 A; 544/192

[56] References Cited

U.S. PATENT DOCUMENTS

| | | | |
|---|---|---|---|
| 2,682,541 | 6/1954 | Kaiser | 260/248 A |
| 2,943,088 | 6/1960 | Westfall | 260/248 A |
| 3,107,244 | 10/1963 | Robertson | 260/248 A |
| 3,956,299 | 5/1976 | Den Otter et al. | 260/248 A |
| 3,969,352 | 7/1976 | Berkowitz | 260/248 A |

*Primary Examiner*—John M. Ford
*Attorney, Agent, or Firm*—William H. Duffey

[57] ABSTRACT

Crude cyanuric acid of improved purity is obtained by pyrolyzing mixtures of urea, recycled cyanuric acid and either ammonium nitrate or concentrated nitric acid at temperatures of about 250° to 300° C.

9 Claims, No Drawings

PRODUCTION OF CYANURIC ACID FROM UREA

BACKGROUND OF THE INVENTION

1. Field of the Invention

The present invention relates to the manufacture of cyanuric acid by the heat treatment of urea. The present invention further relates to a novel continuous process for the preparation of cyanuric acid in high yields and high purity which obviates the conventional acid hydrolysis treatment of the crude cyanuric acid product.

2. Description of the Prior Art

Cyanuric acid, which is the desired end product of the present invention, has the empirical formula $C_3H_3O_3N_3$. It is known to prepare cyanuric acid by a variety of procedures, the most common of which is to merely melt and heat, e.g., pyrolyze technical grade urea at atmospheric pressure above the temperature range at which it decomposes (e.g., 180° C. to 300° C.).

In preparing cyanuric acid by the pyrolysis of urea, however, it is difficult to minimize the production of undesired autocondensation by-products. It is also difficult to obtain the desired cyanuric acid product in good yield and high purity. A cyanuric acid product of high purity is especially important where it is to be utilized as a raw material for other products. Hence, it is necessary to obtain a commercial product substantially free of pyrolytic autocondensation products of urea, and particularly free of amides of cyanuric acid, chiefly ammelide and ammeline.

The pyrolysis of urea may be carried out either in a dry state or in the presence of various inert solvents such as described in U.S. Pat. Nos. 3,065,233; 3,117,968; 3,164,591 and 3,563,987. More recent U.S. Pat. No. 3,810,891 teaches the preparation of cyanuric acid by the pyrolysis of urea or a urea pyrolyzate in an inert polyether solvent at temperatures from about 160° C. to about 220° C. while sparging with an inert gas.

For the most part, however, the use of inert solvents during the pyrolysis of urea still does not achieve a cyanuric acid product of adequate purity for most commerical purposes. To obtain a highly purified product, therefore, it is customary in the art to treat crude cyanuric acid in a strong acid bath with heating, e.g. 3–15% sulfuric acid or hydrochloric acid at nearly 100° C. This acid treatment selectively hydrolyzes the acid-insoluble cyanuric acid amides and converts them to cyanuric acid. Such procedures generally require several hours to complete and further require special acid-resistant holding tanks and centrifuges to hold the acid bath and separate the digested cyanuric acid from the mineral acid. This refining step is known in the art as the "acid digestion step" and is described in U.S. Pat. No. 2,943,088. Suitable acids disclosed in U.S. Pat. No. 2,943,088 for the acid digestion step are hydrochloric, hydrobromic, sulfuric, nitric, phosphoric and various organic acids.

Certain prior art procedures have avoided the acid digestion step by pyrolyzing urea under subatmospheric pressure conditions. Such procedures, however, require additional energy output to maintain the system under vacuum and further can result in substantial loss of urea reactant due to sublimation.

U.S. Pat. No. 2,790,801, which issued Apr. 30, 1957, discloses a relatively simple process for preparing cyanuric acid from urea. Urea is mixed with sulfuric acid and the mixture is heated to about 200° C. Although yields above 90% are said to result, the patentees in U.S. Pat. No. 2,790,801 gave no recognition to ammelide and ammeline impurities which necessarily occur in a product so produced. An acid digestion step, therefore, would still be required to achieve the levels of cyanuric acid purity to meet modern commercial standards. The latter standards are especially rigid if the cyanuric acid is to be later chlorinated.

For the foregoing reasons, it would be desirable to provide an improved process wherein a crude cyanuric acid product can be obtained in high yields and purity from a single pyrolysis reaction without the necessity of maintaining the process under vacuum or subjecting the crude cyanuric acid product to an acid digestion step. This is the primary object of the present invention. Another object of this invention is to provide a crude cyanuric acid product suitable for swimming pool use and for subsequent chlorination with the need for only a minimum of further purification.

SUMMARY OF THE INVENTION

It has now been discovered that a mixture comprising urea, recycled cyanuric acid from the process, and either nitric acid or ammonium nitrate, when heated in a pyrolysis zone to 250°–300° C., will produce high yields of crude cyanuric acid containing surprisingly small amounts of undesirable ammelide and ammeline, e.g. less than 5% total by weight. This compares with ammelide plus ammeline contents of typically 20 weight percent in prior art processes where the customary acid digestion step is omitted, for example, the process taught in U.S. Pat. No. 3,154,545.

DESCRIPTION OF THE INVENTION AND PREFERRED EMBODIMENTS

Although the process of the present invention is especially adapted to continuous operation, it is also advantageous in batch applications.

While not restricted thereto, this invention is conveniently exemplified in connection with a conventional rotating bed pyrolysis kiln. In its simplest form, a rotating pyrolysis kiln can be a hollow, right circular cylinder rotating about its longitudinal axis which axis is disposed horizontally, i.e. substantially parallel (or in some cases partially inclined) with respect to the support base or floor. Rotation of the kiln is achieved through a motor drive system having the necessary speed control and reduction. The kiln drive shaft is conveniently disposed coaxially with the longitudinal axis of the cylindrical kiln.

A pyrolysis kiln is usually open at one end except for an annular flange or lip adjacent to the outside diameter of the kiln. This flange serves to retain the reactants within the hollow kiln as those reactants are centrifuged against the inside wall of the kiln cylindrical periphery. "Flights" are often positioned at various stations along the inside surface of the kiln drum. These "flights" are in the nature of ribs disposed parallel to, or at some angle with respect to, the kiln axis of rotation. Their function is to encourage the centrifuged material within the kiln to roll and tumble as heat is applied to the chamber. The finished product is customarily drawn from the kiln through an exit passage at the opposite end from where the original materials were introduced. A pyrolysis kiln can be heated externally with transverse rows of gas burners disposed at convenient circumferential positions about the outside of the kiln cylinder or drum. In some cases the necessary heat for pyrolysis or calcination is applied internally by suitable means penetrating the open end of the kiln.

The improved crude cyanuric acid product of the present invention is achieved throught the simultaneous calcination or pyrolysis of urea, recycled cyanuric acid and either ammonium nitrate or concentrated (about 65% or 70% concentration in water) nitric acid at pyrolysis temperatures between 250° C. and 300° C., preferably 275°–300° C.

When reference is made herein to "recycled cyanuric acid" or "recycled cyanuric acid from the process", it is intended to embrace, without limitation, typical cyanuric acid obtained from conventional urea pyrolysis processes but such product which has not yet been subjected to acid digestion or acid hydrolysis. The cyanuric acid employed for the recycle portion of this process, therefore, will sometimes contain ammelide plus ammeline totals as high as 10% to 15% by weight or higher. It is to be understood, however, that the recycled cyanuric acid is advantageously employed if its ammelide plus ammeline content is less than 5% to 10%, even 1% or less by weight. Thus, "recycled cyanuric acid" can be fully purified material. It can be newly-added makeup material.

The following examples illustrate the superior cyanuric acid product obtained through the process of the present invention. It will be seen that the addition of optimum amounts of recycled cyanuric acid together with either ammonium nitrate or concentrated nitric acid, has a substantial effect on the chemistry of the urea pyrolysis reaction used to produce crude cyanuric acid. The favorable results are reflected in the high purity of the crude cyanuric acid and, conversely, the low residual ammelide plus ammeline content. Unless otherwise specified, all percentages in the following examples and elsewhere in this specification are expressed as percentages by weight. Percentages expressed for "recycle" or "recycled" cyanuric acid are based upon the weight of urea feed being considered as 100%. Similarly, percentages associated with ammonium nitrate or nitric acid are relative to 100% being the urea feed weight.

Where "parts by weight" are referred to herein, the urea charge is always expressed as 100 parts.

with a base (pH 9.0 to 4.35) for soluble cyanuric acid. Analysis of the crude cyanuric acid reaction product showed 68.3% cyanuric acid and 30.6% ammelide plus ammeline.

EXAMPLE 2

This Example illustrates the improvement in cyanuric acid purity which can be achieved through incorporation of 100% recycled cyanuric acid in the reaction mass. Following the same test procedure and reaction conditions as in Example 1, the reaction vessel was charged with 13 grams of urea and 13 grams of recycled cyanuric acid. The latter contained less than 1% ammelide plus ammeline. Pyrolysis temperature was held at 275° C. for 0.5 hours. Analysis of the reaction product showed 90.6% cyanuric acid and 7.1% ammelide plus ammeline.

EXAMPLE 3

This Example illustrates the outstanding cyanuric acid product which can be achieved according to the process of the present invention. Following the same test procedure as in Example 1, the reaction vessel was charged with 13 grams of urea and 13 grams of recycled cyanuric acid (100% recycled cyanuric acid). The latter contained less than 1% ammelide plus ammeline. In addition, however, there was charged 0.98 grams of ammonium nitrate. The ammonium nitrate charge represented approximately 7.5% of the weight of urea charged to the reaction vessel. Pyrolysis temperature was held at 275° C. for 0.5 hours under ambient pressure conditions. Analysis of the reaction product showed 95.8% cyanuric acid and only 3.4% ammelide plus ammeline.

In further illustration of various embodiments of the process of this invention, the following Table I presents the results of numerous runs following the reaction procedure and process of Example 1 above. Presence of ammonium nitrate and the respective charges of urea and recycled cyanuric acid were varied. Pyrolysis time and pyrolysis temperature were likewise varied. Recycled cyanuric acid is expressed in Table I gravimetrically as well as by percentage recycle based upon urea feed.

TABLE I

| Run No. | Urea (g.) Charge | Recycled Cyanuric Acid (g.) | Ammonium Nitrate (% Urea) | Temp. ° C. | Time (hrs.) | Product Analysis | |
|---|---|---|---|---|---|---|---|
| | | | | | | Cyanuric Acid (%) | Ammelide - Ammeline (%) |
| 1 | 7.8 | 18.2 (234%) | 0 | 275 | 1.5 | 90.3 | 7.5 |
| 2 | 7.8 | 18.2 (234%) | 25.6 | 275 | 1.5 | 98.3 | 0.8 |
| 3 | 13.0 | 13.0 (100%) | 20.0 | 270 | 1.5 | 97.0 | 1.9 |
| 4 | 13.0 | 13.0 (100%) | 15.4 | 270 | 1.5 | 96.5 | 2.6 |
| 5 | 13.0 | 13.0 (100%) | 10.0 | 270 | 1.5 | 95.5 | 3.6 |
| 6 | 7.8 | 18.2 (234%) | 25.6 | 250 | 1.0 | 91.9 | 0.8 |
| 7 | 7.8 | 18.2 (234%) | 20.0 | 300 | 0.25 | 99.6 | 0.4 |
| 8 | 7.8 | 18.2 (234%) | 10.0 | 300 | 0.75 | 99.2 | 0.8 |
| 9 | 20.0 | 6.0 ( 30%) | 10.0 | 300 | 0.75 | 94.7 | 4.4 |
| 10 | 13.0 | 13.0 (100%) | 0 | 250 | 0.75 | 88.9 | 6.4 |

EXAMPLE 1

A substantially closed glass reaction vessel was immersed in an oil bath having means for controlling reaction temperature. The vessel was charged with 26 grams of urea. By controlling the oil bath heating means, the urea pyrolysis temperature was held at 275° C. for 0.5 hours under essentially ambient pressure conditions. After allowing the reaction mass to cool, it was finely ground into powder form using a conventional micro-mill. The ground sample was then analyzed gravimetrically for insoluble cyanuric acid and ammelide plus ammeline content. The sample was titrated Runs 1 and 10 in Table I above, both outside the process of the present invention because of the absence of ammonium nitrate or nitric acid additive, produced a crude cyanuric acid product having the highest ammelide plus ammeline content.

It has been found herein that ammonium nitrate addition levels (based upon urea feed) of 10 to 15% with 75% recycled cyanuric acid (based upon the urea feed), will repeatedly yield a product containing 90% to 95% cyanuric acid. The present process can be carried out by adding the ammonium nitrate separately to the pyrolysis kiln (or other reaction media). In that case the urea, the recycled cyanuric acid and the ammonium nitrate would be individually introduced to the pyrolysis chamber. Alternatively, the ammonium nitrate may be introduced as part of the urea feed proper.

To confirm the findings in Example 1 through 3 and Table I above, a scaled-down pilot plant rotary pyrolysis kiln was constructed according to the following Example 4.

EXAMPLE 4

A stainless steel hollow cylinder, 12.7 cm. in diameter and 15.2 cm. in length, was equipped with a 3.8 centimeter radial depth end-flange or annular retention ring at the feed end of the kiln. This resulted in a 5.1 cm. diameter circular opening on the feed end. The interior of this kiln was provided with four flights each having a height of 0.63 cm. and disposed at 90 degree intervals. The drive end of the kiln was substantially closed which resulted in a kiln capacity of 1500 ml. A glass feed nozzle was attached to a calibrated dropping funnel and adapter tube so that 5 to 7 ml. per minute of melted urea or urea plus ammonium nitrate could be introduced to the kiln bed. The kiln was rotated at speeds up to 50 rpm. Bed temperatures were obtained by means of an iron-constantan thermocouple while the kiln wall temperatures were recorded by means of a radiation pyrometer. The bed consisted either of crude cyanuric acid (approximately 450 grams of −2+4 mesh, assayed 78% cyanuric acid, 22% ammelide plus ammeline) or purified granular cyanuric acid with a purity of 99.5%. The kiln was fed with urea plus 3% water or urea containing 10% ammonium nitrate and 3% water at rates of 6 to 7 ml. per minute. In the pyrolysis of urea plus 10% ammonium nitrate on a bed of purified cyanuric acid (and with no off-gas scrubbing to return cyanuric acid to the system), the purity of the product obtained from this scaled-down rotating kiln reached values of 96% after feeding an equivalent of urea equal to 6.5 bed turnovers. In the pyrolysis of urea on a bed of 78% crude cyanuric acid, the purity reached 92% in the bed and 96% in the ring which developed after three bed turnovers. These purity values agree satisfactorily with pyrolysis data obtained by the procedure of Example 1 above and wherein the recycle cyanuric acid was 75% and the ammonium nitrate additive was present in 10%, both percentages with respect to the urea feed.

EXAMPLE 5

This Example illustrates the improvement in cyanuric acid purity which can be achieved according to the process of the present invention wherein concentrated nitric acid is employed in place of ammonium nitrate within the reaction mass during the pyrolysis operation. The following reactants were mixed together in the dry state on an evaporating dish disposed inside a laboratory-type muffle furnace:

185 g. Urea
55.5 g. Recycled cyanuric acid containing less than 1% ammelide plus ammeline.
27.7 g. Concentrated nitric acid solution (70% nitric acid; 30% water)

Thus, the weight of the recycled cyanuric acid aliquout was 30% of the weight of the urea charge. The weight of the concentrated nitric acid solution was 15% of the weight of the urea charge. The oven temperature was held at 300° C. for 2 hours to achieve substantially complete pyrolysis. After allowing the reaction mass to cool, it was finely ground into powder form and analyzed gravimetrically for insoluble cyanuric acid and ammelide plus ammeline content. The sample was titrated with a base (pH 9.0 to 4.35) for soluble cyanuric acid. Analysis of the crude cyanuric acid reaction product showed 96% cyanuric acid and 3.9% ammelide plus ammeline.

EXAMPLE 6

The procedure of Example 5 was followed except that only 18.5 g. of concentrated nitric acid solution were employed. This represented 10% of the weight of the urea feed. Recycled cyanuric acid was again maintained at 30% of the weight of the urea feed. Analysis of the reaction product after 2 hours at 300° C. showed 94.6% cyanuric acid and 5.4% ammelide plus ammeline.

EXAMPLE 7

Again following the procedure of Example 5, the following reactants were mixed together and disposed within the pyrolysis zone:

185 g. Urea
55 g. Recycled cyanuric acid
16 g. Ammonium nitrate

The ammonium nitrate weight represented 8.6% of the weight of urea feed. Recycled cyanuric acid was again maintained at 30% of the weight of urea feed. The reactants were held at 275° C. for 2 hours. Analysis of the reaction product showed 94.7% cyanuric acid, 5.16% ammelide plus ammeline and 0.1% residual ammonium nitrate.

Using the laboratory furnace procedure of Example 5, various additive combinations were explored. Without using recycled cyanuric acid, it was found that the addition of up to 10% sulfuric acid or nitric acid to the urea (before pyrolysis) produces a crude cyanuric acid (after pyrolysis) which assays about 77–80% cyanuric acid. In similar experiments, the presence of 10% sodium hydroxide during pyrolysis (based on the weight of the urea) reduced the cyanuric acid purity to 35%. The presence of 10% phosphoric acid reduced the purity of the crude cyanuric acid product to 24%.

Again using the laboratory furnace procedure, combinations of recycled cyanuric acid and nitric acid (together with urea feed) produced, after pyrolysis, a crude cyanuric acid product with an assay of over 90%. In comparison, combinations of up to 50% recycled cyanuric acid and 10% sulfuric acid additive produced purities of only 82% in the crude product.

It was found that, in practicing the process of this invention, excessive pyrolysis times may undesirably result in higher ammelide yields together with decreasing cyanuric acid yields. This relationship may be explained by the loss of cyanuric acid as it sublimes, effectively concentrating the ammelide. Cyanuric acid is known to begin to sublime at 250° C. while ammelide will not sublime until 300° C. is reached.

In general, therefore, the sojourn time for the reactants within the pyrolysis zone should be minimized consistent with achieving acceptable cyanuric acid yields. It has been found, for example, that pyrolysis times in the process of this invention which exceed 30 or 40 minutes at 290° to 300° C. can cause excessive sublimation of cyanuric acid accompanied by a negative effect on yield. Longer reaction or sojourn times can be tolerated at lower pyrolysis temperatures, e.g. at 250° C.

Pyrolysis times according to this invention may therefore vary from as little as about 5 minutes up to about 2 hours or more, depending upon other variables in the reaction scheme. Typical pyrolysis reaction times may vary from about 15 minutes to about 90 minutes.

Pyrolysis temperatures in this process should preferably be in the range from about 250° C. to about 300° C. Thus, superior results can still be achieved at, e.g. 240° C. or at 310° C. and these temperatures are within this invention. Pyrolysis temperatures significantly greater than 300° C. may lead to improved cyanuric acid yields. However, the accelerated cyanuric acid sublimation rates may tend to cause a net disadvantage in process economics.

The amount of recycled cyanuric acid within the pyrolysis zone can vary widely as illustrated in Table I above. For example, in Run No. 2 of Table I, 234 parts of recycled cyanuric acid were employed per 100 parts of urea. In Run No. 9, however, only 30 parts were employed per 100 parts of urea. It is therefore seen that the recycled cyanuric acid can be present from a relatively modest amount, e.g. 20 parts, up to more than 200 parts per 100 parts of urea feed. Economic, energy and equipment factors in any given pyrolysis installation will govern to some extent the amount of recycle which can be used. In general, a favorable range is from about 20 parts to about 100 parts, preferably from about 25 parts to 80 parts, all with respect to 100 parts of urea feed.

Optimum presence of either ammonium nitrate or concentrated nitric acid is not the same in each instance. It has been found that the two additives are about equally effective in this process when employed at the same nitrate level. Corrosive tendencies of concentrated nitric acid make ammonium nitrate the preferable additive for this process. Higher concentrations of nitric acid in its aqueous solution, e.g. 90% concentration instead of 65% or 70%, is not found to be advantageous in terms of final purity in the cyanuric acid product.

Thus, the ammonium nitrate or concentrated nitric acid additive is present in the reaction mixture from about 3 to about 40 parts by weight, based upon the weight of urea present, the latter being 100 parts. The preferable range is from about 5 to about 30 parts.

The process of this invention is normally carried out under ambient pressure conditions, i.e. at substantially atmospheric pressure. It is to be understood, however, that somewhat higher or lower pressures can be utilized in the pyrolysis zone without losing the advantages of this process. Maintenance of a small vacuum, e.g. up to 100 mm of mercury gauge, can be beneficial.

When the process of this invention is adapted to continuous operation in a rotating bed pyrolysis kiln, higher effective recycle rates of cyanuric acid can sometimes be achieved by spraying the urea feed (containing the ammonium nitrate additive) onto a bed of cyanuric acid pellets in the kiln.

The presence of water in the reaction mixture up to about 5% of the urea weight can be tolerated without adverse results.

While this invention has been described with respect to specific examples and embodiments, it is to be understood that the invention is not limited thereto and that it can be variously practiced within the scope of the following claims.

The embodiments of this invention in which an exclusive property or privilege is claimed are defined as follows:

1. A process for the manufacture of crude cyanuric acid of improved purity which comprises heating in a pyrolysis zone at a temperature from about 250° C. to about 300° C., a mixture comprising:
    (a) 100 parts by weight of urea;
    (b) from about 20 to about 200 parts by weight, based upon the urea, of recycled cyanuric acid; and
    (c) from about 3 to about 40 parts by weight, based upon the urea, of ammonium nitrate or concentrated nitric acid;
   for a time sufficient to complete the pyrolysis reaction.

2. A process of claim 1 wherein the pyrolysis zone is maintained at substantially atmospheric pressure.

3. A process of claim 1 wherein (c) comprises from about 5 to about 30 parts by weight, based upon the urea, of ammonium nitrate.

4. A process of claim 3 wherein the recycled cyanuric acid (b) is present from about 20 to 100 parts by weight.

5. A process of claim 4 wherein the pyrolysis temperature is 275° to 300° C.

6. A process of claim 4 wherein the heating time is from about 5 minutes to about 2 hours.

7. A continuous process for the manufacture of crude cyanuric acid which comprises the steps of:
    (a) bringing together within a pyrolysis zone:
        (i) 100 parts by weight of urea;
        (ii) from about 20 to about 200 parts by weight, based upon the urea, of recycled cyanuric acid; and
        (iii) from about 5 to about 30 parts by weight, based upon the urea, of ammonium nitrate;
    (b) subjecting the components of (a) above to temperatures of about 250° to about 300° C. for a time sufficient to complete the pyrolysis reaction; and
    (c) removing the crude cyanuric acid product from the pyrolysis zone.

8. A process of claim 7 wherein the pyrolysis reaction time is from about 5 minutes to about 2 hours.

9. A process of claim 8 wherein the pyrolysis zone is maintained at substantially atmospheric pressure.

* * * * *